(12) United States Patent
Aftab

(10) Patent No.: US 9,861,624 B2
(45) Date of Patent: Jan. 9, 2018

(54) METHOD OF TREATING CANCER

(71) Applicant: Exelixis, Inc., South San Francisco, CA (US)

(72) Inventor: Dana T. Aftab, San Rafael, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 14/398,188

(22) PCT Filed: May 2, 2013

(86) PCT No.: PCT/US2013/039284
§ 371 (c)(1),
(2) Date: Oct. 31, 2014

(87) PCT Pub. No.: WO2013/166296
PCT Pub. Date: Nov. 7, 2013

(65) Prior Publication Data
US 2015/0133494 A1    May 14, 2015

Related U.S. Application Data

(60) Provisional application No. 61/641,837, filed on May 2, 2012.

(51) Int. Cl.
*A61K 31/47* (2006.01)

(52) U.S. Cl.
CPC .................... *A61K 31/47* (2013.01)

(58) Field of Classification Search
CPC ..................................... A61K 31/47
USPC ......................................... 514/312
See application file for complete search history.

(56) References Cited

U.S. PATENT DOCUMENTS

| 7,579,473 | B2 | 8/2009 | Bannen et al. |
| 7,977,345 | B2 | 7/2011 | Bannen et al. |
| 7,999,006 | B2 | 8/2011 | Lamb |
| 8,067,436 | B2 | 11/2011 | Bannen et al. |
| 8,178,532 | B2 | 5/2012 | Bannen et al. |
| 8,314,232 | B2 | 11/2012 | Deschamps et al. |
| 8,476,298 | B2 | 7/2013 | Bannen et al. |
| 8,497,284 | B2 | 7/2013 | Bannen et al. |
| 8,673,912 | B2 | 3/2014 | Cannon et al. |
| 8,877,776 | B2 | 11/2014 | Brown et al. |
| 9,174,947 | B2 | 11/2015 | Bannen et al. |
| 2008/0161305 | A1 | 7/2008 | Forsyth et al. |
| 2009/0170896 | A1 | 7/2009 | Bannen et al. |
| 2009/0274693 | A1 | 11/2009 | Gilmer et al. |
| 2011/0077233 | A1 | 3/2011 | Bannen et al. |
| 2012/0070368 | A1 | 3/2012 | Bannen et al. |
| 2012/0184523 | A1 | 7/2012 | Bannen et al. |
| 2012/0252840 | A1 | 10/2012 | Aftab et al. |
| 2012/0282179 | A1 | 11/2012 | Aftab et al. |
| 2013/0030172 | A1 | 1/2013 | Wilson et al. |
| 2013/0142790 | A1 | 6/2013 | Gilmer et al. |
| 2013/0143881 | A1 | 6/2013 | Cannon et al. |
| 2013/0150363 | A1 | 6/2013 | Gilmer et al. |
| 2013/0197230 | A1 | 8/2013 | Wilson et al. |
| 2013/0252940 | A1 | 9/2013 | Bannen et al. |
| 2013/0252956 | A1 | 9/2013 | Kallender et al. |
| 2013/0330377 | A1 | 12/2013 | Wilson |
| 2013/0337015 | A1 | 12/2013 | Wilson et al. |
| 2014/0057908 | A1 | 2/2014 | Smith et al. |
| 2014/0057943 | A1 | 2/2014 | Smith et al. |
| 2014/0066444 | A1 | 3/2014 | Smith et al. |
| 2014/0121239 | A1 | 5/2014 | Aftab |
| 2014/0155396 | A1 | 6/2014 | Bannen et al. |
| 2014/0179736 | A1 | 6/2014 | Schwab et al. |
| 2014/0200242 | A1 | 7/2014 | Wilson |
| 2014/0221372 | A1 | 8/2014 | Kulkarni et al. |
| 2014/0228401 | A1 | 8/2014 | Aftab et al. |
| 2014/0256938 | A1 | 9/2014 | Wilson et al. |
| 2014/0302012 | A1 | 10/2014 | Aftab et al. |
| 2014/0323522 | A1 | 10/2014 | Aftab et al. |
| 2015/0057310 | A1 | 2/2015 | Aftab et al. |
| 2015/0196545 | A1 | 7/2015 | Aftab et al. |
| 2015/0202196 | A1 | 7/2015 | Bannen et al. |
| 2015/0238477 | A1 | 8/2015 | Aftab |
| 2015/0376133 | A1 | 12/2015 | Bannen et al. |
| 2016/0000772 | A1 | 1/2016 | Aftab et al. |
| 2016/0022662 | A1 | 1/2016 | Decillis et al. |
| 2016/0031818 | A1 | 2/2016 | Aftab et al. |
| 2016/0051532 | A1 | 2/2016 | Aftab et al. |

(Continued)

FOREIGN PATENT DOCUMENTS

| WO | 2008076415 | 6/2008 |
| WO | 2009026717 | 3/2009 |

(Continued)

OTHER PUBLICATIONS

Schimmoller, F. et al. "Cabozantinib (XL184), a dual MET-VEGFR2 inhibitor, blocks osteoblastic and osteolytic progression of human prostate cancer xenografts in mouse bone", Molecular Cancer Therapeutics; 23rd AACT-NCI-EORTC International Conference Molecular Targets and Cancer Therapeutics, American Association of Cancer Research, US, San Francisco, CA, US. 10(11) Supp.1, 2011. p. A233.

Aftab et al., "MET and VEGF: synergistic targets in castration-resistant prostate cancer." Clinical and translational oncology, vol. 13, No. 10, pp. 703-709, Nov. 16, 2011.

Chi, K N, et al: "Castration-resistant Prostate Cancer: From New Pathophysiology to New Treatment Targets", European Urology, vol. 56, No. 4, Oct. 1, 2009, pp. 594-605.

Eder, Joseph Paul, et al: 'A phase I study of foretinib, a multi-targeted inhibitor of c-Met and vascular endothelial growth factor receptor 2., Clinical Cancer Research : An Official Journal of the American Association for Cancer Research, vol. 16, No. 13, Jul. 1, 2010 (Jul. 1, 2010), pp. 3507-3516.

Fuller K et al:"The effect of hepatocyte growth factor on the behaviour of osteoclasts." Biochemical and Biophysical Research Communications Jul. 17, 1995, vol. 212, No. 2, Jul. 17, 1995, 334-340.

(Continued)

*Primary Examiner* — Raymond Henley, III
(74) *Attorney, Agent, or Firm* — Honigman Miller Schwartz & Cohn LLP; Heidi M. Berven; Jonathan P. O'Brien

(57) ABSTRACT

This invention is directed to the treatment of cancer, particularly castration-resistant prostate cancer and osteolytic bone metastases, with a dual inhibitor of MET and VEGF.

3 Claims, 3 Drawing Sheets

(56) References Cited

U.S. PATENT DOCUMENTS

| | | | |
|---|---|---|---|
| 2016/0082019 | A1 | 3/2016 | Sweeney et al. |
| 2016/0185725 | A1 | 6/2016 | Bannen et al. |
| 2016/0220554 | A1 | 8/2016 | Smith et al. |
| 2016/0229805 | A1 | 8/2016 | Wilson et al. |
| 2017/0057921 | A1 | 3/2017 | Wilson et al. |
| 2017/0143689 | A1 | 5/2017 | Wilson et al. |

FOREIGN PATENT DOCUMENTS

| | | |
|---|---|---|
| WO | 2009036055 | 3/2009 |
| WO | 2009140549 | 11/2009 |
| WO | 2010039248 | 4/2010 |
| WO | 2011017639 | 2/2011 |
| WO | 2012031027 | 3/2012 |
| WO | 2012044572 | 4/2012 |
| WO | 2012044577 | 4/2012 |
| WO | 2012064967 | 5/2012 |
| WO | 2012151326 | 11/2012 |

OTHER PUBLICATIONS

Hussain et al.:"Cabozantinib (XL184)in metastatic castration-resistant prostate cancer (mCRPC): Results from a phase II randomized discontinuation trial." ASCO Meeting Abstracts Jun. 9, 2011.

International Search Report for PCT/US2012/036191, dated Jul. 6, 2012.

International Search Report for PCT/US2012/056281, dated Dec. 19, 2012.

International Search Report for PCT/US2012/064116, dated Jan. 16, 2013.

Kitagawa Yasuhide et al: "Vascular endothelial growth factor contributes to prostate cancer-mediated osteoblastic activity", Cancer Research, vol. 65, No. 23, Dec. 2005 (Dec. 1, 2005), pp. 10921-10929.

Kurzrock, R., et al., "Activity of XL184 (Cabozantinib), an oral tyrosine kinase inhibitor, in patients with medullary thyroid cancer", Journal of Clinical Oncology, vol. 29, No. 19, pp. 2660-2666, Jul. 1, 2011.

Kuznar W: "Cabozantinib shows dramatic effects on bone metastases in advanced prostate cancer", American Health and Drug Benefits 2011 Engage Healthcare Communications, Inc. USA, vol. 4, No. 4 Spec. Issue, Aug. 2011.

Lazner, F. et al., "Osteopetrosis and osteoporosis: two sides of the same coin", Human Molecular Genentics, vol. 8, No. 10, pp. 1839-1846, 1999.

Lee, et al., "A Dose-Ranging Study of Cabozantinib in Men with Castration-Resistant Prostate Cancer and Bone Metastases", Clinical Cancer Research, vol. 19, No. 11, pp. 3088-3094, Jun. 1, 2013 (Jun. 1, 2013).

Mohamedali Khalid A et al: "Inhibition of prostate tumor growth and bone remodeling by the vascular targeting VEGF(121)/rGel", Cancer Research, vol. 66, No. 22, Nov. 2006 (Nov. 2006), pp. 10919-10928.

Nakashiro, et al., "Role of androgen receptor (AR) and c-Met/HGF receptor in androgen-independent prostate cancer", 3. Proceedings of the Japanese Cancer Association, vol. 62, pp. 218-219, 2003.

Navab, et al., "Co-overexpression of MET and Hepatocyte Growth Factor Promotes Systemic Metastasis in NCI-H460 Non-Small Cell Lung Carcinoma Cells", Neoplasia, vol. 11, No. 12, pp. 1292-1300, Dec. 31, 2009.

Nechushtan et al., 22nd EORTC-NCI-AACR Symposium on molecular targets and cancer therapeutics, Nov. 16-19, 2010, Berlin, Germany.

Nenonen, a., et al., "Serum TRACP 5b Is a Useful Marker for Monitoring Alendronate Treatment: Comparison With Other Markers of Bone Turnover", Journal of Bone and Mineral Research, vol. 20, No. 8, pp. 1804-1812, Apr. 4, 2005.

Ono, et al., "Involvement of hepatocyte growth factor in the development of bone metastasis of a mouse mammary cancer cell line, BALB/c-MC", Bone, vol. 39, pp. 27-34, Feb. 3, 2006.

Qian, Fawn, et al: Inhibition of tumor cell growth, invasion, and metastasis by EXEL-2880 (XL880, GSK1363089), a novel inhibitor of HGF and VEGF receptor tyrosine kinasesn, Cancer Research, American Association for Cancer Research, US, vol. 69, No. 20, Oct. 15, 2009 (Oct. 15, 2009), pp. 8009-8016.

Saylor, Philip J, et al: "Emerging therapies to prevent skeletal morbidity in men with prostate cancer", Journal of Clinical Oncology, Lippincott Williams & Wilkins, USA, vol. 29, No. 27, Sep. 20, 2011, pp. 3705-3714.

Smith, D. C., et al., "406 Phase 2 study of XL184 in a cohort of patients (pts) with castration resistant prostate cancer (CRPC) and measurable soft tissue disease", European Journal of Cancer. Supplement, vol. 8, No. 7, Nov. 1, 2010 (Nov. 1, 2010), p. 129.

Susa, et al., "Src inhibitors: drugs for the treatment of osteoporosis, cancer or both?" TiPS, vol. 21, pp. 489-495, Dec. 2000.

Vaishampayan, Ulka, "Cabozantinib as a Novel Therapy for Renal Cell Carcinoma", Curr. Oncol. Rep., vol. 15, pp. 76-82, Jan. 5, 2013.

Wu Yichao et al: "Novel agents and new therapeutics in castration-resistant prostate cancer.", Current Opinion in Oncology vol. 23, No. 3, May 2011 (May 2011), pp. 290-296. Section "XL184"; p. 294.

Yang, Q., et al: "VEGF enhancement of osteoclast survival and bone resorption involves VEGF receptor-2 signaling and beta3-integrin", Matrix Biology, Elsevier, NL, vol. 27, No. 7, Sep. 1, 2008 (Sep. 1, 2008), pp. 589-599.

METHOD OF TREATING CANCER

CROSS-REFERENCE TO RELATED APPLICATIONS

This application is a United States National Phase filing of PCT/US2013/039284, filed May 2, 2013, which claims the benefit of priority of U.S. Provisional Application No. 61/641,837, filed May 2, 2012, all of which are incorporated herein by reference.

FIELD OF THE INVENTION

This invention is directed to the treatment of cancer, particularly castration-resistant prostate cancer and osteolytic bone metastases, with a dual inhibitor of MET and VEGF.

BACKGROUND OF THE INVENTION

Castration-Resistant Prostate Cancer (CRPC) is a leading cause of cancer-related death in men. Despite progress in systemic therapy for CRPC, improvements in survival are modest, and virtually all patients succumb to this disease within about 2 years. The primary cause of morbidity and mortality in CRPC is metastasis to the bone, which occurs in about 90% of cases.

Metastasis to the bone is a complex process that involves interactions between cancer cells and components of the bone microenvironment including osteoblasts, osteoclasts, and endothelial cells. Bone metastases cause local disruption of normal bone remodeling, and lesions generally show a propensity for either osteoblastic (bone-forming) or osteolytic (bone-resorbing) activity. Although most CRPC patients with bone metastases display features of both types of lesions, prostate cancer bone metastases are often osteoblastic, with abnormal deposition of unstructured bone accompanied by increased skeletal fractures, spinal cord compression, and severe bone pain.

The receptor tyrosine kinase MET plays important roles in cell motility, proliferation, and survival, and it has been shown to be a key factor in tumor angiogenesis, invasiveness, and metastasis. Prominent expression of MET has been observed in primary and metastatic prostate carcinomas, with evidence for higher levels of expression in bone metastases compared to lymph node metastases or primary tumors.

Vascular endothelial growth factor (VEGF) and its receptors on endothelial cells are widely accepted as key mediators in the process of tumor angiogenesis. In prostate cancer, elevated VEGF in either plasma or urine is associated with shorter overall survival. VEGF may also play a role in activating the MET pathway in tumor cells by binding to neuropilin-1, which is frequently unregulated in prostate cancer and appears to activate MET in a co-receptor complex. Agents targeting the VEGF signaling pathway have demonstrated some activity in patients with CRPC.

MET signalling can influence osteoblast and osteoclast function. Strong immunohistochemical staining of MET has been observed in osteoblasts in developing bone, while both HGF and MET are expressed by osteoblasts and osteoclasts in vitro and regulate cellular responses such as proliferation, migration and differentiation. Secretion of HGF by osteoblasts has been proposed as a key factor in osteoblast/osteoclast coupling [58] and is thought to promote the development of bone metastases by tumour cells that express MET.

Like MET, the VEGF signalling pathway is strongly implicated in bone formation and remodelling. Both osteoblasts and osteoclasts express VEGF and VEGF receptors, which appear to be involved in autocrine and/or paracrine feedback mechanisms regulating cell proliferation, migration, differentiation and survival. Experiments using genetically modified mice have shown that angiogenesis and VEGF signalling in osteoblasts are both important in bone development and repair.

Thus, a need remains for methods of treating prostate cancer, including CRPC and the associated osteolytic bone metastases.

SUMMARY OF THE INVENTION

These and other needs are met by the present invention which is directed to a method for treating bone cancer associated with prostate cancer. The method comprises administering a therapeutically effective amount of a compound that modulates both MET and VEGF to a patient in need of such treatment. In one embodiment, the bone cancer is osteolytic bone metastases. In a further embodiment, the prostate cancer is CRPC. In a further embodiment, the bone cancer is osteolytic bone metastases associated with CRPC.

In one aspect, the present invention is directed to a method for treating osteolytic bone metastases, CRPC, or osteolytic bone metastases associated with CRPC, comprising administering a therapeutically effective amount of a compound that dually modulates MET and VEGF to a patient in need of such treatment.

In one embodiment of this and other aspects, the dual acting MET/VEGF inhibitor is a compound of Formula I

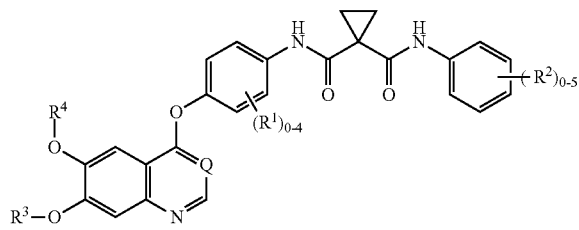

or a pharmaceutically acceptable salt thereof, wherein:
$R^1$ is halo;
$R^2$ is halo;
$R^3$ is $(C_1-C_6)$alkyl;
$R^4$ is $(C_1-C_6)$alkyl; and
Q is CH or N.

In another embodiment, the compound of Formula I is a compound of Formula Ia

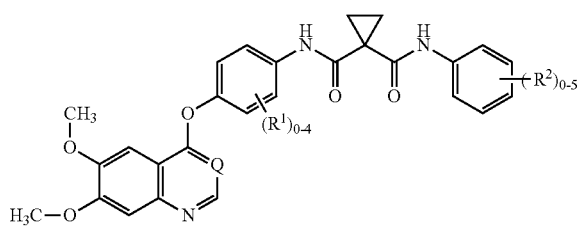

or a pharmaceutically acceptable salt thereof, wherein:

R¹ is halo;
R² is halo; and
Q is CH or N.

In another embodiment, the compound of Formula I is compound 1:

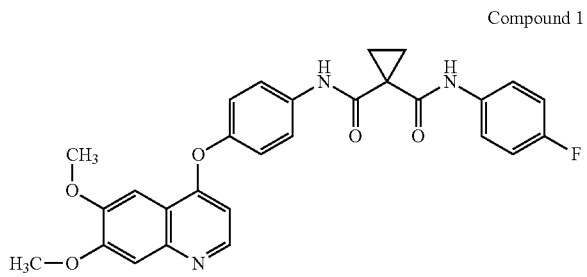 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof. Compound 1 is known as N-(4-{[6,7-bis(methyloxy)quinolin-4-yl]oxy}phenyl)-N'-(4-fluorophenyl)cyclopropane-1,1-dicarboxamide.

In another embodiment, the compound of Formula I, Ia, or Compound 1 is administered as a pharmaceutical composition comprising a pharmaceutically acceptable additive, diluent, or excipient.

In another aspect, the invention provides a method for treating osteolytic bone metastases associated with CRPC, comprising administering a therapeutically effective amount of a pharmaceutical composition comprising Compound of Formula I or the malate salt of Compound of Formula I or another pharmaceutically acceptable salt of Formula I, to a patient in need of such treatment. In a specific embodiment, the Compound of Formula I is Compound 1.

In another aspect, the invention provides a method for reducing or stabilizing metastatic bone lesions associated with CRPC, comprising administering a therapeutically effective amount of a pharmaceutical composition comprising Compound of Formula I, Ia or the malate salt of Compound of Formula I or another pharmaceutically acceptable salt of Compound of Formula I, to a patient in need of such treatment. In a specific embodiment, the Compound of Formula I is Compound 1.

In another aspect, the invention provides a method for reducing bone pain due to metastatic bone Lesions associated with CRPC, comprising administering a therapeutically effective amount of a pharmaceutical composition comprising Compound of Formula I or the malate salt of Compound of Formula I or another pharmaceutically acceptable salt of Compound of Formula I, to a patient in need of such treatment. In a specific embodiment, the Compound of Formula I is Compound 1.

In another aspect, the invention provides a method for treating or minimizing bone pain due to metastatic bone lesions associated with CRPC, comprising administering a therapeutically effective amount of a pharmaceutical composition comprising Compound of Formula I or the malate salt of Compound of Formula I or another pharmaceutically acceptable salt of Compound of Formula I, to a patient in need of such treatment. In a specific embodiment, the Compound of Formula I is Compound 1.

In another aspect, the invention provides a method for strengthening bones in patients with metastatic bone lesions associated with CRPC, comprising administering a therapeutically effective amount of a pharmaceutical composition comprising Compound of Formula I or the malate salt of Compound of Formula I or another pharmaceutically acceptable salt of Compound of Formula I, to a patient in need of such treatment. In a specific embodiment, the Compound of Formula I is Compound 1. Bone strengthening can occur when the disruption in normal bone remodeling due to bone metastases is minimized, for instance by administering a Compound of Formula I as provided herein.

In another aspect, the invention provides a method for preventing osteolytic bone metastases associated with CRPC, comprising administering a therapeutically effective amount of a pharmaceutical composition comprising Compound of Formula I or the malate salt of Compound of Formula I or another pharmaceutically acceptable salt of Compound of Formula I, to a patient in need of such treatment. In a specific embodiment, the Compound of Formula I is Compound 1.

In another aspect, the invention provides a method for preventing osteolytic bone metastases in patients with prostate cancer who are castration resistant but have not yet advanced to metastatic disease, comprising administering a therapeutically effective amount of a pharmaceutical composition comprising Compound of Formula I or the malate salt of Compound of Formula I or another pharmaceutically acceptable salt of Compound of Formula I, to a patient in need of such treatment. In a specific embodiment, the Compound of Formula I is Compound 1.

In another aspect, the invention provides a method for extending the overall survival in patients with CRPC with osteolytic bone metastases, comprising administering a therapeutically effective amount of a pharmaceutical composition comprising Compound of Formula I or the malate salt of Compound of Formula I or another pharmaceutically acceptable salt of Compound of Formula I, to a patient in need of such treatment.

In these and other aspects, the ability of the compound of Formula I to treat, ameliorate, or reduce the severity of bone metastases can be determined both qualitatively and quantitatively using various physiological markers, such as circulating tumor cell (CTC), Cross-linked C-terminal telopeptides of type-1 collagen (CTx), and Cross-linked N-terminal telopeptides of type-1 collagen (NTx) counts and imaging technologies. The imaging technologies include positron emission tomography (PET) or computerized tomography (CT) and magnetic resonance imaging. By using these imaging techniques, it is possible to monitor and quantify the reduction in tumor size and the reduction in the number and size of bone lesions in response to treatment with the compound of Formula I.

In these and other aspects, shrinkage of soft tissue and visceral lesions has been observed result when the compound of Formula I is administered to patients with CRPC. Moreover, administration of the compound of Formula I leads to increases in hemoglobin concentration in patients CRPC patients with anemia.

DETAILED DESCRIPTION OF THE INVENTION

Abbreviations and Definitions

Figure 1:
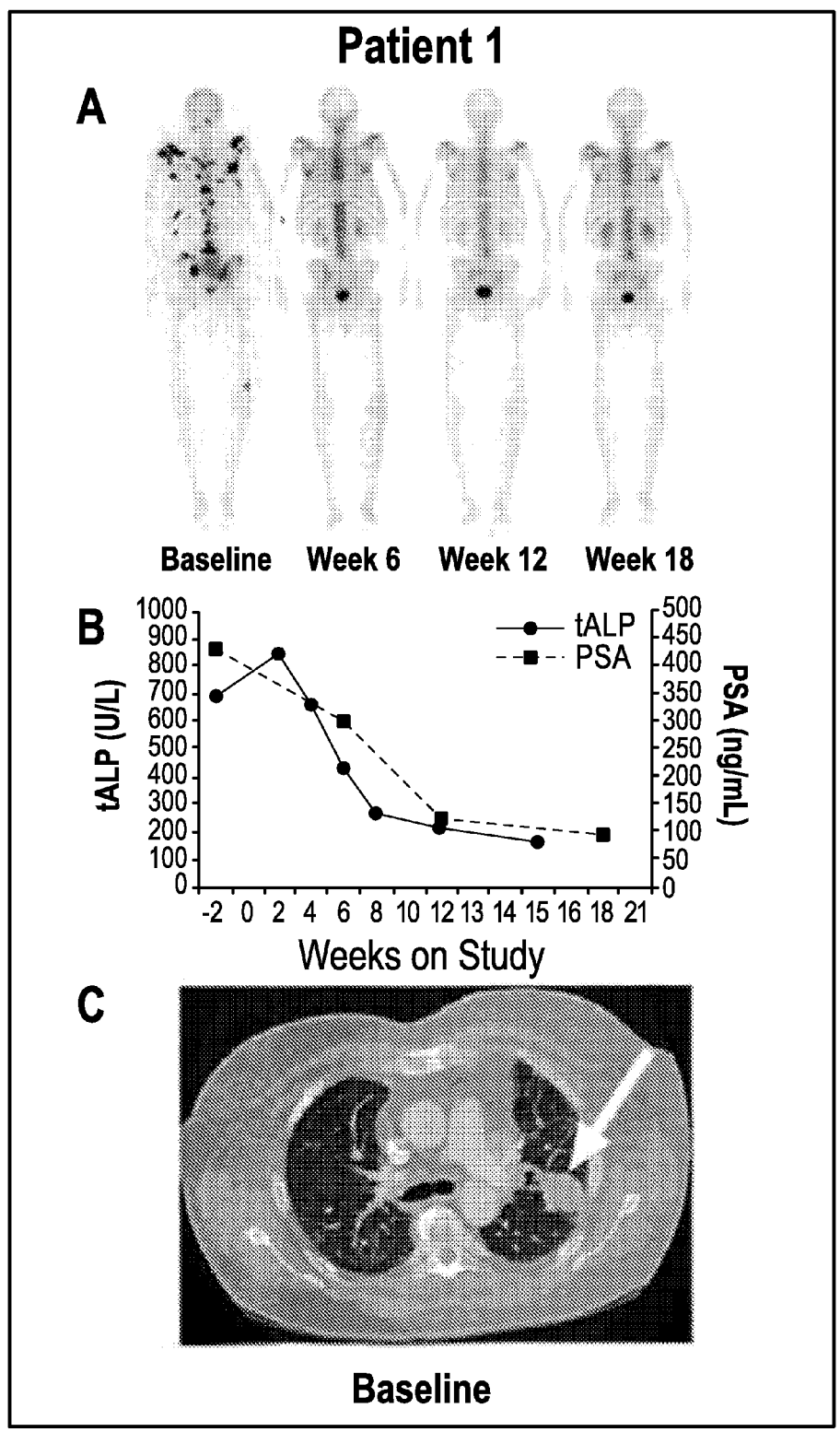
FIGS. 1A-C show the bone scan (FIG. 1A), bone scan response (FIG. 1B), and CT scan data (FIG. 1C) for Patient 1.

The following abbreviations and terms have the indicated meanings throughout:

| Abbreviation | Meaning |
| --- | --- |
| Ac | Acetyl |
| bALP | Bone-specific alkaline phosphatase |
| Br | Broad |
| ° C. | Degrees Celsius |
| c- | Cyclo |
| CBZ | CarboBenZoxy = benzyloxycarbonyl |
| CTx | Cross-linked C-terminal telopeptides of type-1 collagen |
| d | Doublet |
| dd | Doublet of doublet |
| dt | Doublet of triplet |
| DCM | Dichloromethane |
| DME | 1,2-dimethoxyethane |
| DMF | N,N-Dimethylformamide |
| DMSO | dimethyl sulfoxide |
| Dppf | 1,1'-bis(diphenylphosphano)ferrocene |
| EI | Electron Impact ionization |
| G | Gram(s) |
| h or hr | Hour(s) |
| HPLC | High pressure liquid chromatography |
| L | Liter(s) |
| M | Molar or molarity |
| m | Multiplet |
| Mg | Milligram(s) |
| MHz | Megahertz (frequency) |
| Min | Minute(s) |
| mL | Milliliter(s) |
| μL | Microliter(s) |
| μM | Micromole(s) or micromolar |
| mM | Millimolar |
| Mmol | Millimole(s) |
| Mol | Mole(s) |
| MS | Mass spectral analysis |
| N | Normal or normality |
| nM | Nanomolar |
| NMR | Nuclear magnetic resonance spectroscopy |
| NTx | Cross-linked N-terminal telopeptides of type-1 collagen |
| q | Quartet |
| RT | Room temperature |
| s | Singlet |
| t or tr | Triplet |
| TFA | Trifluoroacetic acid |
| THF | Tetrahydrofuran |
| TLC | Thin layer chromatography |

The symbol "—" means a single bond, "=" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

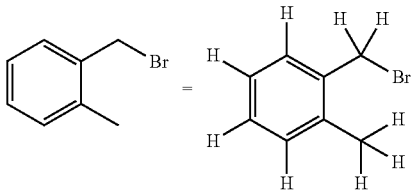

If a group "R" is depicted as "floating" on a ring system, as for example in the formula:

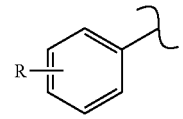

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

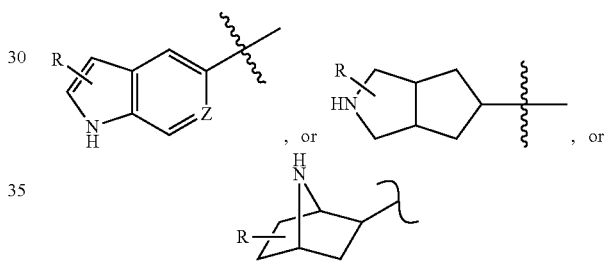

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, as for example in the formula:

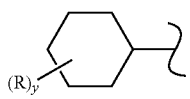

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

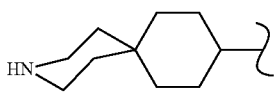

"Halogen" or "halo" refers to fluorine, chlorine, bromine or iodine.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, malic acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, ameliorates a symptom of the disease. A therapeutically effective amount is intended to include an amount of a compound alone or in combination with other active ingredients effective to modulate c-Met, and/or VEGFR2, or effective to treat or prevent cancer. The amount of a compound of the invention which constitutes a "therapeutically effective amount" will vary depending on the compound, the disease state and its severity, the age of the patient to be treated, and the like. The therapeutically effective amount can be determined by one of ordinary skill in the art having regard to their knowledge and to this disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experience.

Embodiments

In one embodiment the compound of Formula I is the compound of Formula Ia:

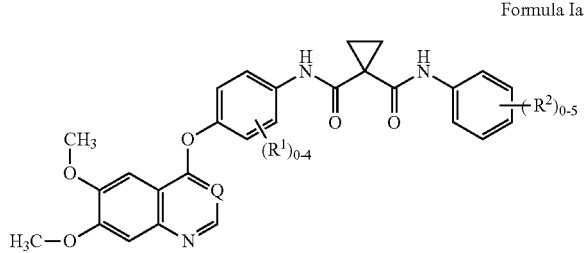

Formula Ia or a pharmaceutically acceptable salt thereof, wherein:
$R^1$ is halo;
$R^2$ is halo; and
Q is CH or N.

In another embodiment, the compound of Formula I is Compound 1:

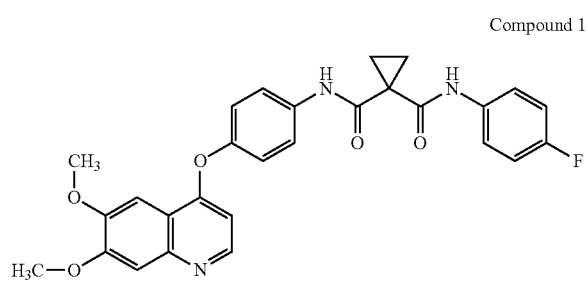 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof. As indicated previously, compound 1 is referred to herein as N-(4-{[6,7-bis(methyloxy)quinolin-4-yl]oxy}phenyl)-N'-(4-fluorophenyl)cyclopropane-1,1-dicarboxamide. WO 2005/030140 discloses Compound 1 and describes how it is made (Example 37, 38, and 48) and also discloses the therapeutic activity of this compound to inhibit, regulate and/or modulate the signal transduction of kinases, (Assays, Table 4, entry 289). Example 48 is on paragraph [0353] in WO 2005/030140, the entire contents of which is incorporated herein by reference.

In other embodiments, the compound of Formula I, Ia, or Compound 1, or a pharmaceutically acceptable salt thereof, is administered as a pharmaceutical composition, wherein the pharmaceutical composition additionally comprises a pharmaceutically acceptable carrier, excipient, or diluent. In a specific embodiment, the Compound of Formula I is Compound 1.

The compound of Formula I, Formula Ia and Compound I, as described herein, includes both the recited compounds as well as individual isomers and mixtures of isomers. In each instance, the compound of Formula I includes the pharmaceutically acceptable salts, hydrates, and/or solvates of the recited compounds and any individual isomers or mixture of isomers thereof.

In other embodiments, the compound of Formula I, Ia, or Compound 1 can be the (L)-malate salt. The malate salt of the Compound of Formula I and of Compound 1 is disclosed in WO 2010/083414 and US 2012/0070368, the entire contents of each of which are incorporated herein by reference.

In other embodiments, the compound of Formula I can be the malate salt.

In other embodiments, the compound of Formula I can be the (D)-malate salt.

In other embodiments, the compound of Formula I can be the (L)-malate salt.

In other embodiments, the compound of Formula Ia can be the malate salt.

In other embodiments, the compound of Formula Ia can be the (D)-malate salt.

In other embodiments, the compound of Formula Ia can be the (L)-malate salt.

In other embodiments, Compound 1 can be the malate salt.

In other embodiments, Compound 1 can be the (D)-malate salt.

In other embodiments, Compound 1 can be the (L)-malate salt.

In another embodiment, the malate salt is in the crystalline N-1 form of the (L) malate salt and/or the (D) malate salt of the Compound 1 as disclosed in US 2012/0070368, the entire contents of which is incorporated herein by reference. Also see WO 2008/083319, the entire contents of which is incorporated herein by reference, for the properties of crystalline enantiomers, including the N-1 and/or the N-2 crystalline forms of the malate salt of Compound 1. Methods of making and characterizing such forms are fully described in WO 2010/083414, which is incorporated herein by reference in its entirety.

In another embodiment, the invention is directed to a method for ameliorating the symptoms of osteolytic bone metastases, comprising administering to a patient in need of such treatment a therapeutically effective amount of a compound of Formula I in any of the embodiments disclosed herein. In a specific embodiment, the Compound of Formula I is Compound 1.

In another embodiment, the compound of Formula I is administered post-taxotere treatment. In a specific embodiment, the Compound of Formula I is Compound 1.

In another embodiment, the compound of Formula I is as effective or more effective than mitoxantrone plus prednisone. In a specific embodiment, the Compound of Formula I is Compound 1.

In another embodiment, the Compound of Formula I, Ia, or Compound 1 or a pharmaceutically acceptable salt thereof is administered orally once daily as a tablet or capsule.

In another embodiment, Compound 1 is administered orally as its free base or malate salt as a capsule or tablet.

In another embodiment, Compound 1 is administered orally once daily as its free base or as the malate salt as a capsule or tablet containing up to 100 mg of Compound 1.

In another embodiment, Compound 1 is administered orally once daily as its free base or as the malate salt as a capsule or tablet containing 100 mg of Compound 1.

In another embodiment, Compound 1 is administered orally once daily as its free base or as the malate salt as a capsule or tablet containing 95 mg of Compound 1.

In another embodiment, Compound 1 is administered orally once daily as its free base or as the malate salt as a capsule or tablet containing 90 mg of Compound 1.

In another embodiment, Compound 1 is administered orally once daily as its free base or as the malate salt as a capsule or tablet containing 85 mg of Compound 1.

In another embodiment, Compound 1 is administered orally once daily as its free base or as the malate salt as a capsule or tablet containing 80 mg of Compound 1.

In another embodiment, Compound 1 is administered orally once daily as its free base or as the malate salt as a capsule or tablet containing 75 mg of Compound 1.

In another embodiment, Compound 1 is administered orally once daily as its free base or as the malate salt as a capsule or tablet containing 70 mg of Compound 1.

In another embodiment, Compound 1 is administered orally once daily as its free base or as the malate salt as a capsule or tablet containing 65 mg of Compound 1.

In another embodiment, Compound 1 is administered orally once daily as its free base or as the malate salt as a capsule or tablet containing 60 mg of Compound 1.

In another embodiment, Compound 1 is administered orally once daily as its free base or as the malate salt as a capsule or tablet containing 55 mg of Compound 1.

In another embodiment, Compound 1 is administered orally once daily as its free base or as the malate salt as a capsule or tablet containing 50 mg of Compound 1.

In another embodiment, Compound 1 is administered orally once daily as its free base or as the malate salt as a capsule or tablet containing 45 mg of Compound 1.

In another embodiment, Compound 1 is administered orally once daily as its free base or as the malate salt as a capsule or tablet containing 40 mg of Compound 1.

In another embodiment, Compound 1 is administered orally once daily as its free base or as the malate salt as a capsule or tablet containing 30 mg of Compound 1.

In another embodiment, Compound 1 is administered orally once daily as its free base or as the malate salt as a capsule or tablet containing 25 mg of Compound 1.

In another embodiment, Compound 1 is administered orally once daily as its free base or as the malate salt as a capsule or tablet containing 20 mg of Compound 1.

In another embodiment, Compound 1 is administered orally once daily as its free base or as the malate salt as a capsule or tablet containing 15 mg of Compound 1.

In another embodiment, Compound 1 is administered orally once daily as its free base or as the malate salt as a capsule or tablet containing 10 mg of Compound 1.

In another embodiment, Compound 1 is administered orally once daily as its free base or as the malate salt as a capsule or tablet containing 5 mg of Compound 1.

In another embodiment, Compound 1 is administered as its free base or malate salt orally once daily as a tablet as provided in the following table.

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In another embodiment, Compound 1 is administered orally as its free base or malate salt once daily as a tablet as provided in the following table.

| Ingredient | (% w/w) |
| --- | --- |
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, Compound 1 is administered orally as its free base or malate salt once daily as a tablet as provided in the following table.

| Ingredient | Theoretical Quantity (mg/unit dose) |
| --- | --- |
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

Any of the tablet formulations provided above can be adjusted according to the dose of Compound 1 desired. Thus, the amount of each of the formulation ingredients can be proportionally adjusted to provide a table formulation containing various amounts of Compound 1 as provided in the previous paragraphs. In another embodiment, the formulations can contain 20, 40, 60, or 80 mg of Compound 1.

Administration

Administration of the compound of Formula I, Formula Ia, or Compound 1, or a pharmaceutically acceptable salt thereof, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin dosages (which can be in capsules or tablets), powders, solutions, suspensions, or aerosols, or the like, specifically in unit dosage forms suitable for simple administration of precise dosages.

The compositions will include a conventional pharmaceutical carrier or excipient and a compound of Formula I as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compound of Formula I may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of composition depends on various factors such as the mode of drug administration (e.g., for oral administration, compositions in the form of tablets, pills or capsules) and the bioavailability of the drug substance. Recently, pharmaceutical compositions have been developed especially for drugs that show poor bioavailability based upon the principle that bioavailability can be increased by increasing the surface area i.e., decreasing particle size. For example, U.S. Pat. No. 4,107,288 describes a pharmaceutical composition having particles in the size range from 10 to 1,000 nm in which the active material is supported on a crosslinked matrix of macromolecules. U.S. Pat. No. 5,145,684 describes the production of a pharmaceutical composition in which the drug substance is pulverized to nanoparticles (average particle size of 400 nm) in the presence of a surface modifier and then dispersed in a liquid medium to give a pharmaceutical composition that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the compound of Formula I, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administration are, for example, suppositories that can be prepared by mixing the compound of Formula I with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of the compound of Formula I include ointments, powders, sprays, and inhalants. The active component is admixed under sterile conditions with a physiologically acceptable carrier and any preservatives, buffers, or propellants as may be required. Ophthalmic compositions, eye ointments, powders, and solutions are also contemplated as being within the scope of this disclosure.

Compressed gases may be used to disperse the compound of Formula I in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of Formula I, or a pharmaceutically acceptable salt thereof, and 99% to 1% by weight of a suitable pharmaceutical excipient. In one example, the composition will be between about 5% and about 75% by weight of a compound(s) of Formula I, Formula Ia, or Compound 1, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of Formula I, or a pharmaceutically acceptable salt thereof, for treatment of a disease-state in accordance with the teachings of this disclosure.

The compounds of this disclosure, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compound of Formula I, Formula Ia, or Compound 1, can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

In other embodiments, the compound of Formula I, Formula Ia, or Compound 1, can be administered to the patient concurrently with other cancer treatments. Such treatments include other cancer chemotherapeutics, hormone replacement therapy, radiation therapy, or immunotherapy, among others. The choice of other therapy will depend on a number of factors including the metabolic stability and length of action of the compound, the age, body weight, general health, sex, diet, mode and time of administration, rate of excretion, drug combination, the severity of the particular disease-states, and the host undergoing therapy.

Preparation of Compound 1

Preparation of N-(4-{[6,7-bis(methyloxy)quinolin-4-yl]oxy}phenyl)-N'-(4-fluorophenyl)cyclopropane-1,1-dicarboxamide and the (L)-malate salt thereof.

The synthetic route used for the preparation of N-(4-[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1:

was deemed complete (approximately 9.0 hours) when less than 2 percent of the starting material remained (in process high-performance liquid chromotography [HPLC] analysis). The reaction mixture was cooled to approximately 10° C. and then quenched into a chilled solution of dichloromethane (DCM, 238.0 kg), 30% NH₄OH (135.0 kg), and ice (440.0 kg). The resulting mixture was warmed to approximately 14° C., and phases were separated. The organic phase was washed with water (40.0 kg) and concentrated by vacuum distillation to remove the solvent (approximately 190.0 kg). Methyl-t-butyl ether (MTBE, 50.0 kg) was added to the batch, and the mixture was cooled to approximately 10° C., during which time the product crystallized out. The solids were recovered by centrifugation, washed with n heptane (20.0 kg), and dried at approximately 40° C. to afford the title compound (8.0 kg).

Preparation of 6,7-Dimethyl-4-(4-nitro-phenoxy)-quinoline

A reactor was sequentially charged with 4-chloro-6,7-dimethoxy-quinoline (8.0 kg), 4 nitrophenol (7.0 kg), 4

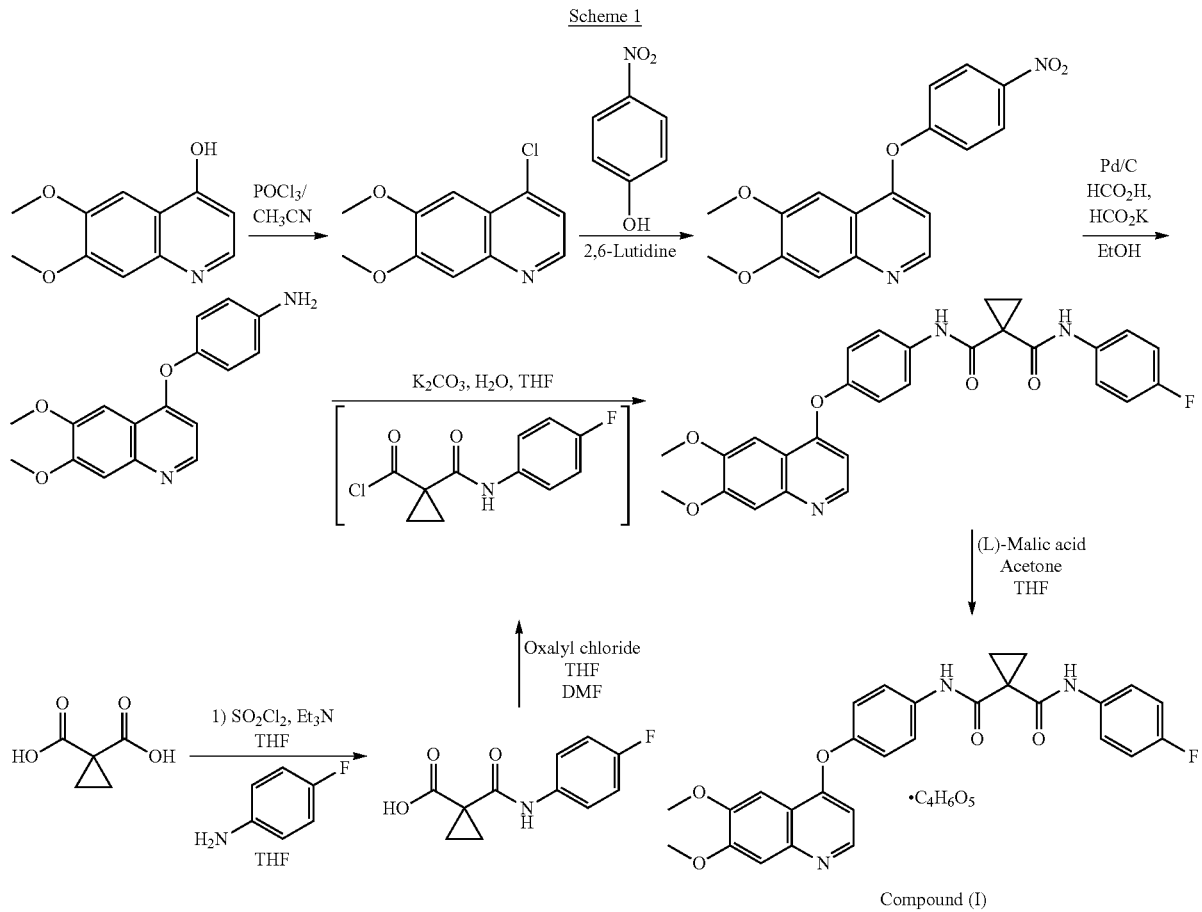

Scheme 1

Compound (I)

Preparation of 4-Chloro-6,7-dimethoxy-quinoline

A reactor was charged sequentially with 6,7-dimethoxy-quinoline-4-ol (10.0 kg) and acetonitrile (64.0 L). The resulting mixture was heated to approximately 65° C. and phosphorus oxychloride (POCl₃, 50.0 kg) was added. After the addition of POCl₃, the temperature of the reaction mixture was raised to approximately 80° C. The reaction dimethylaminopyridine (0.9 kg), and 2,6 lutidine (40.0 kg). The reactor contents were heated to approximately 147° C. When the reaction was complete (less than 5 percent starting material remaining as determined by in process HPLC analysis, approximately 20 hours), the reactor contents were allowed to cool to approximately 25° C. Methanol (26.0 kg) was added, followed by potassium carbonate (3.0 kg) dissolved in water (50.0 kg). The reactor contents were stirred for approximately 2 hours. The resulting solid precipitate was filtered, washed with water (67.0 kg), and dried at 25° C. for approximately 12 hours to afford the title compound (4.0 kg).

Preparation of
4-(6,7-Dimethoxy-quinoline-4-yloxy)-phenylamine

A solution containing potassium formate (5.0 kg), formic acid (3.0 kg), and water (16.0 kg) was added to a mixture of 6,7-dimethoxy-4-(4-nitro-phenoxy)-quinoline (4.0 kg), 10 percent palladium on carbon (50 percent water wet, 0.4 kg) in tetrahydrofuran (THF, 40.0 kg) that had been heated to approximately 60° C. The addition was carried out such that the temperature of the reaction mixture remained approximately 60° C. When the reaction was deemed complete as determined using in-process HPLC analysis (less than 2 percent starting material remaining, typically 15 hours), the reactor contents were filtered. The filtrate was concentrated by vacuum distillation at approximately 35° C. to half of its original volume, which resulted in the precipitation of the product. The product was recovered by filtration, washed with water (12.0 kg), and dried under vacuum at approximately 50° C. to afford the title compound (3.0 kg; 97 percent area under curve (AUC)).

Preparation of 1-(4-Fluoro-phenylcarbamoyl)-cyclopropanecarboxylic acid

Triethylamine (8.0 kg) was added to a cooled (approximately 4° C.) solution of commercially available cyclopropane-1,1-dicarboxylic acid (2 l, 10.0 kg) in THF (63.0 kg) at a rate such that the batch temperature did not exceed 10° C. The solution was stirred for approximately 30 minutes, and then thionyl chloride (9.0 kg) was added, keeping the batch temperature below 10° C. When the addition was complete, a solution of 4-fluoroaniline (9.0 kg) in THF (25.0 kg) was added at a rate such that the batch temperature did not exceed 10° C. The mixture was stirred for approximately 4 hours and then diluted with isopropyl acetate (87.0 kg). This solution was washed sequentially with aqueous sodium hydroxide (2.0 kg dissolved in 50.0 L of water), water (40.0 L), and aqueous sodium chloride (10.0 kg dissolved in 40.0 L of water). The organic solution was concentrated by vacuum distillation followed by the addition of heptane, which resulted in the precipitation of solid. The solid was recovered by centrifugation and then dried at approximately 35° C. under vacuum to afford the title compound. (10.0 kg).

Preparation of
1-(4-Fluoro-phenylcarbamoyl)-cyclopropanecarbonyl chloride

Oxalyl chloride (1.0 kg) was added to a solution of 1-(4-fluoro-phenylcarbamoyl)-cyclopropanecarboxylic acid (2.0 kg) in a mixture of THF (11 kg) and N, N-dimethylformamide (DMF; 0.02 kg) at a rate such that the batch temperature did not exceed 30° C. This solution was used in the next step without further processing.

Preparation of N-(4-{[6,7-bis(methyloxy)quinolin-4-yl]oxy}phenyl)-N'-(4-fluorophenyl)cyclopropane-1,1-dicarboxamide The solution from the previous step containing 1-(4-fluoro-phenylcarbamoyl)-cyclopropanecarbonyl chloride was added to a mixture of 4-(6,7-dimethoxy-quinoline-4-yloxy)-phenylamine (3.0 kg) and potassium carbonate (4.0 kg) in THF (27.0 kg) and water (13.0 kg) at a rate such that the batch temperature did not exceed 30° C. When the reaction was complete (in typically 10 minutes), water (74.0 kg) was added. The mixture was stirred at 15-30° C. for approximately 10 hours, which resulted in the precipitation of the product. The product was recovered by filtration, washed with a pre-made solution of THF (11.0 kg) and water (24.0 kg), and dried at approximately 65° C. under vacuum for approximately 12 hours to afford the title compound (free base, 5.0 kg). $^1$H NMR (400 MHz, d$_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15 (m, 2H), 6.4 (s, 1H), 4.0 (d, 6H), 1.5 (s, 4H). LC/MS: M+H=502.

Preparation of N-(4-{[6,7-bis(methyloxy)quinolin-4-yl]oxy}phenyl)-N'-(4-fluorophenyl)cyclopropane-1,1-dicarboxamide, (L) malate salt A solution of L-malic acid (2.0 kg) in water (2.0 kg) was added to a solution of Cyclopropane-1,1-dicarboxylic acid [4-(6,7-dimethoxy-quinoline-4-yloxy)-phenyl]-amide (4-fluoro-phenyl)-amide free base (15, 5.0 kg) in ethanol, maintaining a batch temperature of approximately 25° C. Carbon (0.5 kg) and thiol silica (0.1 kg) were then added, and the resulting mixture was heated to approximately 78° C., at which point water (6.0 kg) was added. The reaction mixture was then filtered, followed by the addition of isopropanol (38.0 kg), and was allowed to cool to approximately 25° C. The product was recovered by filtration and washed with isopropanol (20.0 kg), and dried at approximately 65° C. to afford the title compound (5.0 kg).

Alternative Preparation of N-(4-{[6,7-Bis(methyloxy)quinolin-4-yl]oxy}phenyl)-N'-(4-fluorophenyl)cyclopropane-1,1-dicarboxamide and the (L)-malate salt thereof An alternative synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 2.

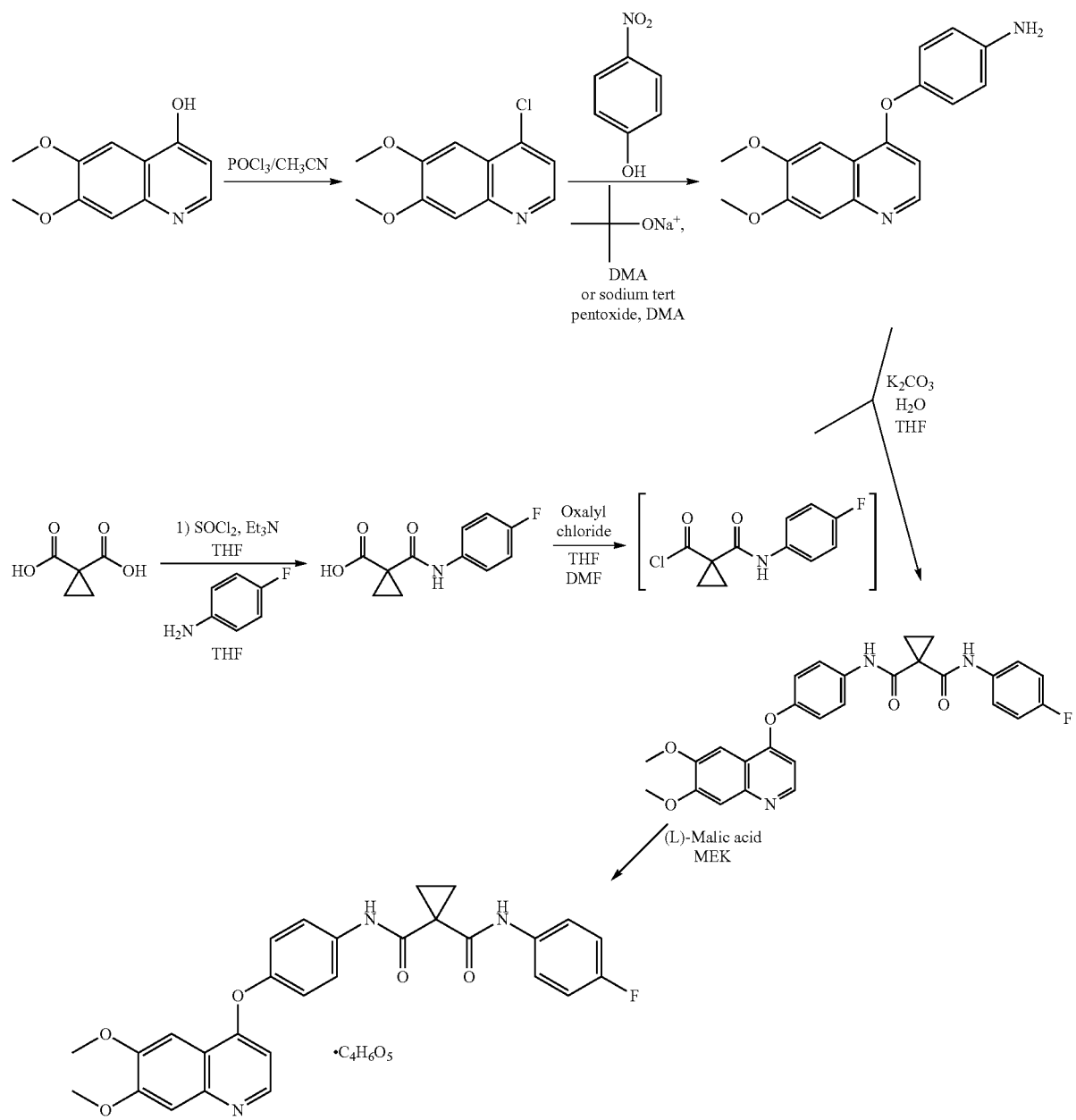

Scheme 2

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C. and phosphorus oxychloride (POCl₃, 130.6 kg) was added. After the addition of POCl₃, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2-7° C. and then quenched into a chilled solution of dichloromethane (DCM, 482.8 kg), 26 percent NH₄OH (251.3 kg), and water (900 L). The resulting mixture was warmed to approximately 20-25° C., and phases were separated. The organic phase was filtered through a bed of AW hyflo super-cel NF (Celite; 5.4 kg) and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate which was then filtered and washed with n-heptane (92.0 kg), and dried on a filter at approximately 25° C. under nitrogen to afford the title compound. (35.6 kg).

Preparation of
4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg) and DMA (167.2 kg) at 20-25° C. This mixture was then heated to 100-105° C. for approximately 13 hours. After the reaction was deemed complete as determined using in-process HPLC analysis (less than 2 percent starting material remaining), the reactor contents were cooled at 15-20° C. and water (pre-cooled, 2-7° C., 587 L) charged at a rate to maintain 15-30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0-5° C. and aged for approximately 1 hour after which time the solid was filtered, washed with THF (147.6 kg) and dried on a filter under vacuum at approximately 25° C. to yield 4-(6,7-dimethoxy-quinoline-4-yloxy)-phenylamine (34.0 kg).

Alternative Preparation of
4-(6,7-Dimethoxy-quinoline-4-yloxy)-phenylamine 4-chloro-6,7-dimethoxyquinoline (34.8 kg) and 4-aminophenol (30.8 kg) and sodium tert pentoxide (1.8 equivalents) 88.7 kg, 35 weight percent in THF) were charged to a reactor, followed by N,N-dimethylacetamide (DMA, 293.3 kg). This mixture was then heated to 105-115° C. for approximately 9 hours. After the reaction was deemed complete as determined using in-process HPLC analysis (less than 2 percent starting material remaining), the reactor contents were cooled at 15-25° C. and water (315 kg) was added over a two hour period while maintaining the temperature between 20-30° C. The reaction mixture was then agitated for an additional hour at 20-25° C. The crude product was collected by filtration and washed with a mixture of 88 kg water and 82.1 kg DMA, followed by 175 kg water. The product was dried on a filter drier for 53 hours. The LOD showed less than 1 percent w/w.

In an alternative procedure, 1.6 equivalents of sodium tert-pentoxide were used and the reaction temperature was increased from 110-120° C. In addition, the cool down temperature was increased to 35-40° C. and the starting temperature of the water addition was adjusted to 35-40° C., with an allowed exotherm to 45° C.

Preparation of
1-(4-Fluorophenylcarbamoyl)-cyclopropanecarboxylic acid

Triethylamine (19.5 kg) was added to a cooled (approximately 5° C.) solution of cyclopropane-1,1-dicarboxylic acid (24.7 kg) in THF (89.6 kg) at a rate such that the batch temperature did not exceed 5° C. The solution was stirred for approximately 1.3 hours, and then thionyl chloride (23.1 kg) was added, keeping the batch temperature below 10° C. When the addition was complete, the solution was stirred for approximately 4 hours keeping temperature below 10° C. A solution of 4-fluoroaniline (18.0 kg) in THF (33.1 kg) was then added at a rate such that the batch temperature did not exceed 10° C. The mixture was stirred for approximately 10 hours after which the reaction was deemed complete. The reaction mixture was then diluted with isopropyl acetate (218.1 kg). This solution was washed sequentially with aqueous sodium hydroxide (10.4 kg, 50 percent dissolved in 119 L of water) further diluted with water (415 L), then with water (100 L) and finally with aqueous sodium chloride (20.0 kg dissolved in 100 L of water). The organic solution was concentrated by vacuum distillation (100 L residual volume) below 40° C. followed by the addition of n-heptane (171.4 kg), which resulted in the precipitation of solid. The solid was recovered by filtration and washed with n-heptane (102.4 kg), resulting in wet, crude 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C. followed by the addition of water (320 L) resulting in slurry which was recovered by filtration, washed sequentially with water (20 L) and n-heptane (103.1 kg) and then dried on the filter at approximately 25° C. under nitrogen to afford the title compound (25.4 kg).

Preparation of
1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of
1-(4-Fluoro-phenylcarbamoyl)-cyclopropanecarbonyl chloride A reactor was charged with 1-(4-fluoro-phenylcarbamoyl)-cyclopropanecarboxylic acid (35 kg), 344 g DMF, and 175 kg THF. The reaction mixture was adjusted to 12-17° C. and then to the reaction mixture was charged 19.9 kg of oxalyl chloride over a period of 1 hour. The reaction mixture was left stirring at 12-17° C. for 3 to 8 hours. This solution was used in the next step without further processing.

Preparation of cyclopropane-1,1-dicarboxylic acid
[4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20-25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by 412.9 kg THF. To the reaction mixture was charged a solution of 48.3 $K_2CO_3$ in 169 kg water. The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20-30° C. over a minimum of two hours. The reaction mixture was stirred at 20-25° C. for a minimum of three hours. The reaction temperature was then adjusted to 30-25° C. and the mixture was agitated. The agitation was stopped and the phases of the mixture were allowed to separate. The lower aqueous phase was removed and discarded. To the remaining upper organic phase was added 804 kg water. The reaction was left stirring at 15-25° C. for a minimum of 16 hours.

The product precipitated. The product was filtered and washed with a mixture of 179 kg water and 157.9 kg THF in two portions. The crude product was dried under a vacuum for at least two hours. The dried product was then taken up in 285.1 kg THF. The resulting suspension was transferred to reaction vessel and agitated until the suspension became a clear (dissolved) solution, which required heating to 30-35° C. for approximately 30 minutes. 456 kg water was then added to the solution, as well as 20 kg SDAG-1 ethanol (ethanol denatured with methanol over two hours. The mixture was agitated at 15-25° C. fir at least 16 hours. The product was filtered and washed with a mixture of 143 kg water and 126.7 THF in two portions. The product was dried at a maximum temperature set point of 40° C.

In an alternative procedure, the reaction temperature during acid chloride formation was adjusted to 10-15° C. The recrystallization temperature was changed from 15-25° C. to 45-50° C. for 1 hour and then cooled to 15-25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, malate salt Cyclopropane-1,1-dicarboxylic acid [4-(6,7-dimethoxy-quinoline-4-yloxy)-phenyl]-amide (4-fluoro-phenyl)-amide (1-5; 13.3 kg), L-malic acid (4.96 kg), methyl ethyl ketone (MEK; 188.6 kg) and water (37.3 kg) were charged to a reactor and the mixture was heated to reflux (approximately 74° C.) for approximately 2 hours. The reactor temperature was reduced to 50 to 55° C. and the reactor contents were filtered. These sequential steps described above were repeated two more times starting with similar amounts of starting material (13.3 kg), L-Malic acid (4.96 kg), MEK (198.6 kg) and water (37.2 kg). The combined filtrate was azeotropically dried at atmospheric pressure using MEK (1133.2 kg) (approximate residual volume 711 L; KF≤0.5% w/w) at approximately 74° C. The temperature of the reactor contents was reduced to 20 to 25° C. and held for approximately 4 hours resulting in solid precipitate which was filtered, washed with MEK (448 kg) and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2), 658.2 kg methyl ethyl ketone, and 129.1 kg water (37.3 kg) were charged to a reactor and the mixture was heated 50-55° C. for approximately 1-3 hours, and then at 55-60° C. for an addition al 4-5 hours. The mixture was clarified by filtration through a 1 μm cartridge. The reactor temperature was adjusted to 20-25° C. and vacuum distilled with a vacuum at 150-200 mm Hg with a maximum jacket temperature of 55° C. to the volume range of 558-731 L.

The vacuum distillation was performed two more times with the charge of 380 kg and 380.2 kg methyl ethyl ketone, respectively. After the third distillation, the volume of the batch was adjusted to 18 v/w of cyclopropane-1,1-dicarboxylic acid [4-(6,7-dimethoxy-quinoline-4-yloxy)-phenyl]-amide (4-fluoro-phenyl)-amide by charging 159.9 kg methyl ethyl ketone to give a total volume of 880 L. An addition al vacuum distillation was carried out by adjusting 245.7 methyl ethyl ketone. The reaction mixture was left with moderate agitation at 20-25° C. for at least 24 hours. The product was filtered and washed with 415.1 kg methyl ethyl ketone in three portions. The product was dried under a vacuum with the jacket temperature set point at 45° C.

In an alternative procedure, the order of addition was changed so that a solution of 17.7 kg L-malic acid dissolved in 129.9 kg water was added to cyclopropane-1,1-dicarboxylic acid [4-(6,7-dimethoxy-quinoline-4-yloxy)-phenyl] amide (4-fluoro-phenyl)-amide (48.7 kg) in methyl ethyl ketone (673.3 kg).

Case Studies

The MET and VEGF signaling pathways appear to play important roles in osteoblast and osteoclast function. Strong immunohistochemical staining of MET has been observed in both cell types in developing bone. HGF and MET are expressed by osteoblasts and osteoclasts in vitro and mediate cellular responses such as proliferation, migration, and expression of ALP. Secretion of HGF by osteoblasts has been proposed as a key factor in osteoblast/osteoclast coupling, and in the development of bone metastases by tumor cells that express MET. Osteoblasts and osteoclasts also express VEGF and its receptors, and VEGF signaling in these cells is involved in potential autocrine and/or paracrine feedback mechanisms regulating cell migration, differentiation, and survival.

Bone metastases are present in 90 percent of patients with castration-resistant prostate cancer (CRPC), causing significant morbidity and mortality. Activation of the MET and VEGFR signaling pathways is implicated in the development of bone metastases in CRPC. Three metastatic CRPC patients treated with Compound 1, an inhibitor of MET and VEGFR, had dramatic responses with near complete resolution of bone lesions, marked reduction in bone pain and total serum alkaline phosphatase (tALP) levels, and reduction in measurable disease. These results indicate that dual modulation of the MET and VEGFR signaling pathways is a useful therapeutic approach for treating CRPC.

Compound 1 is an orally bioavailable multitargeted tyrosine kinase inhibitor with potent activity against MET and VEGFR2. Compound 1 suppresses MET and VEGFR2 signaling, rapidly induces apoptosis of endothelial cells and tumor cells, and causes tumor regression in xenograft tumor models. Compound 1 also significantly reduces tumor invasiveness and metastasis and substantially improves overall survival in a murine pancreatic neuroendocrine tumor model. In a phase 1 clinical study, Compound 1 was generally well-tolerated, with fatigue, diarrhea, anorexia, rash, and palmar-plantar erythrodysesthesia being the most commonly observed adverse events.

Based on target rationale and observed antitumor activity in clinical studies, an adaptive phase 2 trial was undertaken in multiple indications including CRPC (http://clinicaltrials.gov/ct2/results?term=NCT00940225 for Study NCT00940225 last visited Sep. 20, 2011)), in which Compound 1 was administered as a 100 mg dose to patients. The findings in the first three CRPC patients with evidence of bone metastases on bone scan enrolled to this study are described in the following Case Studies.

Baseline characteristics for patients 1-3 are summarized in Table 1.

TABLE 1

Summary of Baseline Characteristics and Preliminary Best Responses for CRPC Patients Treated with Compound 1.

| Baseline Characteristics | Patient 1 | Patient 2 | Patient 3 |
| --- | --- | --- | --- |
| Age (years) | 77 | 73 | 66 |
| Diagnosis | 1993 | 2009 | 2009 |
| ECOG performance status | 1 | 0 | 1 |
| Disease location(s) | Lung, LN, bone | Liver, LN, bone | LN, bone |
| Prior cancer therapies | Radical prostatectomy, radiation to prostate bed, CAB, DES, docetaxel | Radiation to pubic ramus and acetabulum, CAB | CAB, docetaxel |
| Bisphophonates | No | No | Yes |
| Narcotics | Yes | No | No |
| Pain | Yes | Yes | Yes |
| PSA (ng/mL) | 430.4 | 14.7 | 2.8 |
| tALP (U/L) | 689 | 108 | 869 |
| Hemoglobin (g/dL) | 13.5 | 13.3 | 10.2 |
| Summary of Best Responses | | | |
| Tumor response | −41% | −20% | −51% |
| Bone scan | Complete resolution | Improvement | Near resolution |
| Pain | Improvement | Pain-free | Pain-free |
| PSA | −78% | +61% | −57% |
| tALP | −77% | −6% | −77% |
| Hemoglobin (g/dL) | +1.4 | +1.8 | +2.2 |

ADT, androgen-deprivation therapy;
CAB, combined androgen blockade (leuprolide + bicalutamide);
DES, diethylstilbestrol;
LN, lymph node;
PSA, prostate-specific antigen;
tALP, total alkaline phosphatase.

Patient 1 was diagnosed with localized prostate cancer in 1993 and treated with radical prostatectomy (Gleason score unavailable; PSA, 0.99 ng/mL). In 2000, local disease recurrence was treated with radiation therapy. In 2001, combined androgen blockade (CAB) with leuprolide and bicalutamide was initiated for rising PSA (3.5 ng/mL). In 2006, diethystillbestrol (DES) was administered briefly. In 2007, 6 cycles of docetaxel were given for new lung metastases. Rising PSA was unresponsive to antiandrogen withdrawal. Androgen ablation therapy was continued until clinical progression. In October 2009, bone metastasis to the spine associated with impingement on the spinal cord and back pain, was treated with radiation therapy (37.5 Gy). In February 2010, a bone scan was performed due to increasing bone pain and showed diffuse uptake of radiotracer in the axial and appendicular skeleton. A CT scan revealed new pulmonary and mediastinal lymph node metastases. PSA was 430.4 ng/mL.

Patient 2 was diagnosed in April of 2009 after presenting with a pathologic fracture (Gleason score, 4+5=9; PSA, 45.34 ng/mL). Bone scan showed uptake of radiotracer in the left iliac wing, left sacroiliac joint, femoral head, and the pubic symphysis. Biopsy of the left pubic ramus confirmed metastatic adenocarcinoma with mixed lytic and blastic lesions. CAB with leuprolide and bicalutamide and radiation therapy (8 Gy) to the left pubic ramus and acetabulum resulted in bone pain relief and PSA normalization. Rising PSA in November 2009 (16 ng/mL) was unresponsive to antiandrogen withdrawal. In February 2010, bone scan showed multiple foci throughout the axial and appendicular skeleton. A CT scan revealed retroperitoneal lymph node enlargement and liver metastases (PSA, 28.1 ng/mL). Further progression of disease was marked by recurrent bone pain, new lung and hepatic metastases.

Patient 3 was diagnosed in April 2009 after presenting with right hip pain (Gleason score, 4+5=9; PSA, 2.6 ng/mL). Bone scan showed uptake of radiotracer at multiple sites throughout the axial and appendicular skeleton. A CT scan revealed retroperitoneal, common iliac, and supraclavicular adenopathy. CAB with leuprolide and bicalutamide was initiated. The patient received 6 cycles of docetaxel through December 2009. Following treatment, a bone scan showed no changes. A CT scan revealed near resolution of the retroperitoneal and common iliac adenopathy. In March 2010, PSA began to rise, and bone pain worsened. A repeat bone scan showed new foci, and a CT scan showed an increase in the retroperitoneal, para-aortic, and bilateral common iliac adenopathy. Rising PSA in April 2010 (2.8 ng/mL) and increasing bone pain were unresponsive to antiandrogen withdrawal.

Results

All patients provided informed consent before study screening.

Patient 1 started Compound 1 on Feb. 12, 2010. Four weeks later, significant reduction in bone pain was reported. At Week 6, bone scan showed a dramatic decrease in radiotracer uptake by bone metastases (FIG. 1A). A CT scan showed a partial response (PR) with a 33% decrease in measurable target lesions (FIG. 1C). At Week 12, near complete resolution of bone lesions and a 44% decrease in target lesions was observed and was stable through Week 18. Corresponding with the bone scan response, after an initial rise, serum tALP levels decreased from 689 U/L at baseline to 159 U/L at Week 18 (FIG. 1B and Table 1). In addition, there was an increase in hemoglobin of 1.4 g/dL at Week 2 compared with baseline (Table 1). PSA decreased from 430 ng/mL at baseline to 93.5 ng/mL at Week 18 (FIG. 1B and Table 1). The patient was on open-label treatment through Week 18 when he withdrew after developing Grade 3 diarrhea.

Figure 2:
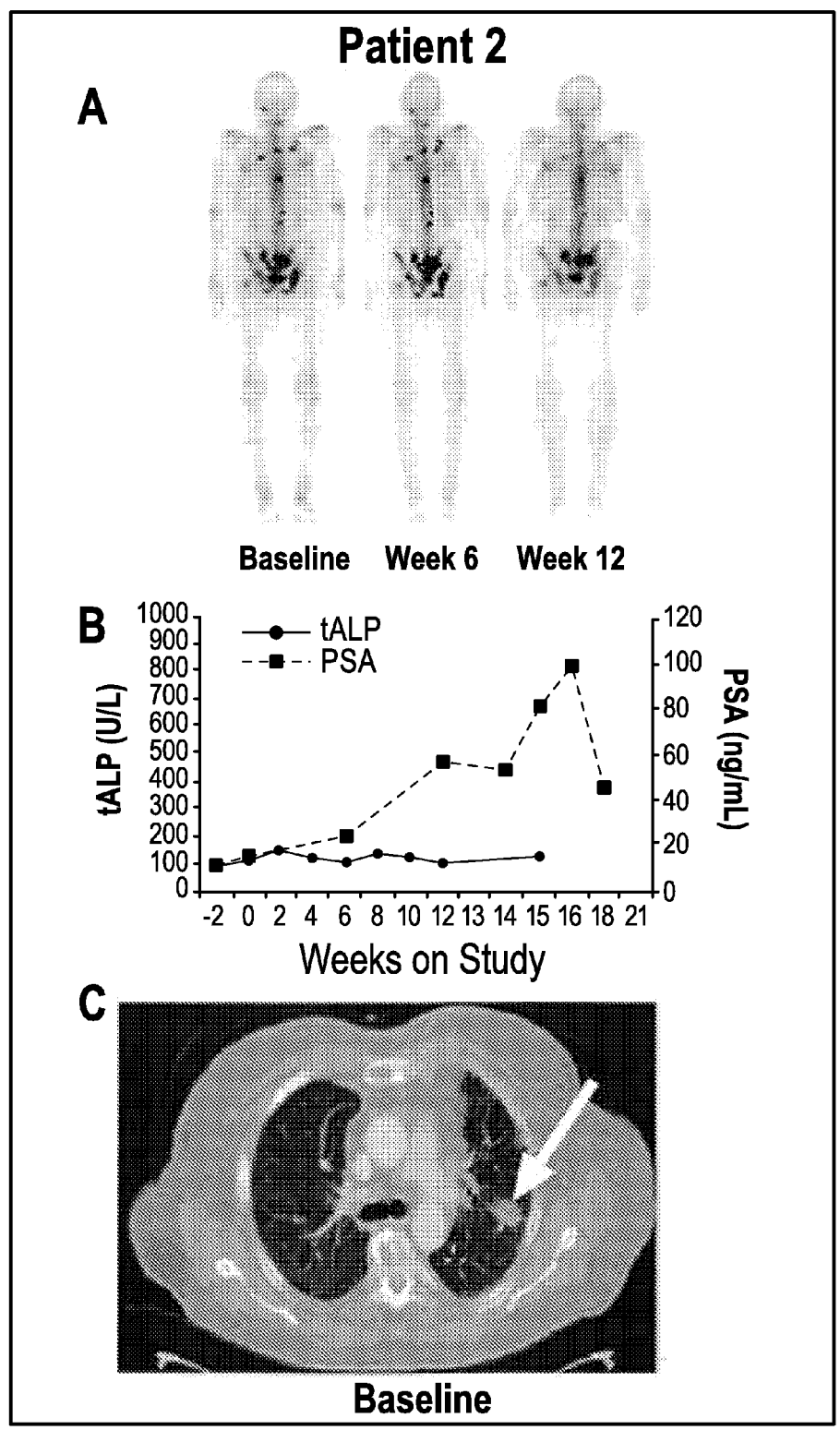
FIGS. 2A-C show the bone scan (FIG. 2A), bone scan response (FIG. 2B), and CT scan data (FIG. 2C) for Patient 2.

Patient 2 started Compound 1 on Mar. 31, 2010. At Week 4, reduction in bone pain was reported. At Week 6, bone scan showed a slight flair in radiotracer uptake by bone lesions (FIG. 2A), and a CT scan showed a 13% decrease in target lesions (FIG. 2C). At Week 12, a substantial reduction of radiotracer uptake (FIG. 2A) and a 20% decrease in measurable disease were observed (Table 1). After randomization to placebo at Week 12 the patient developed severe bone pain and sacral nerve root impingement. Radiation to the spine was administered, and the patient crossed over to open-label Compound 1 treatment at Week 15. Serum tALP levels were within the normal range (101-144 U/L) (FIG. 2B). Hemoglobin increased by 1.8 g/dL at Week 12 compared with baseline (Table 1). PSA peaked at close to 6-fold of baseline by Week 16, but then decreased to 2-fold of baseline by Week 18 subsequent to crossing over to Compound 1 from placebo (FIG. 2B and Table 1). The patient continues on Compound 1 treatment as of September 2010.

Figure 3:
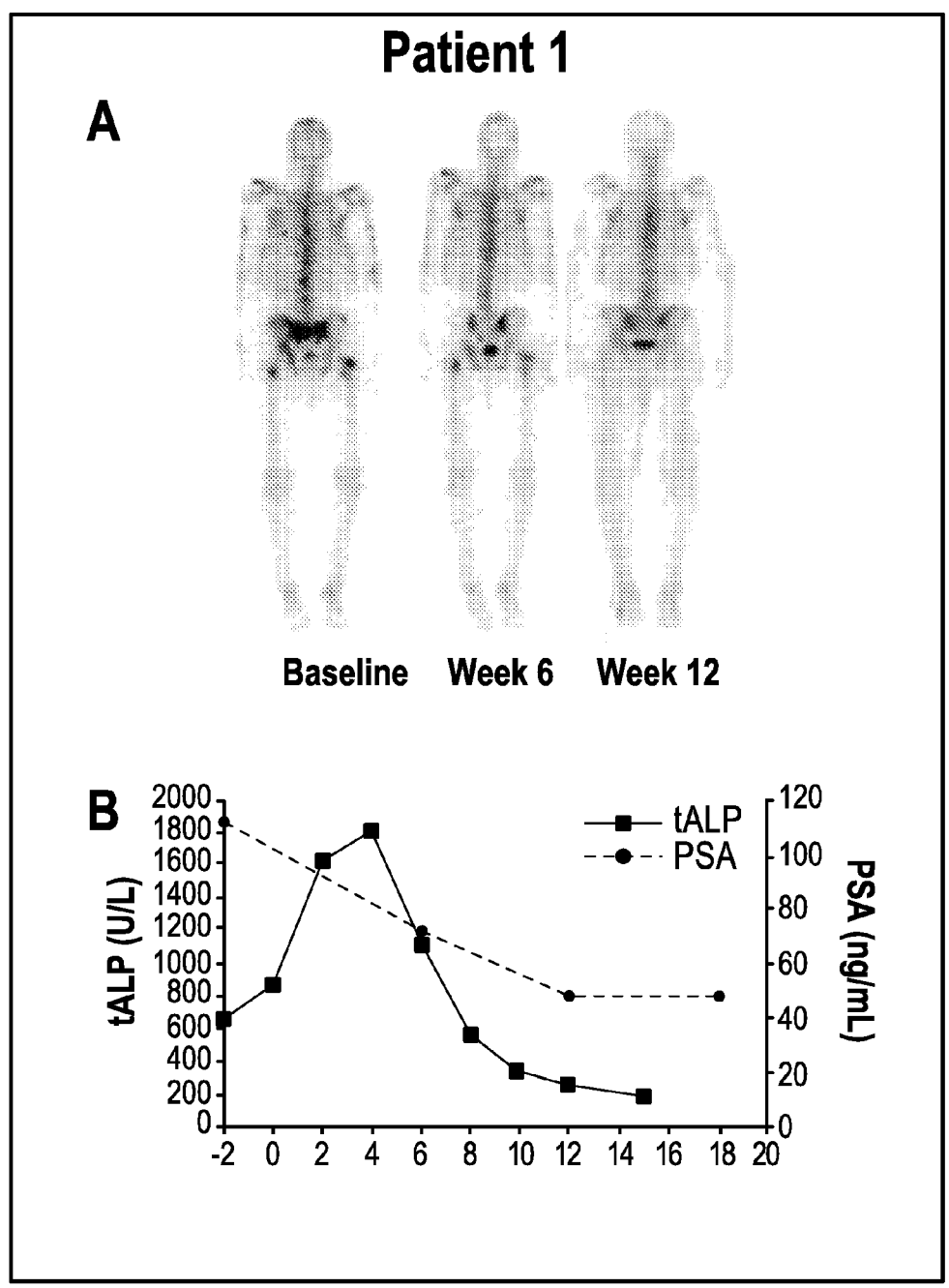
FIGS. 3A-B show the bone scan (FIG. 3A), bone scan response (FIG. 3B) for Patient 3.

Patient 3 started Compound 1 on Apr. 26, 2010. After three weeks a complete resolution of pain was reported. At Week 6, bone scan showed a dramatic reduction in radiotracer uptake (FIG. 3A), and a CT scan showed a PR with a 43% decrease in measurable target lesions. At Week 12 a complete resolution of bone lesions on bone scan (FIG. 3A) and a 51% decrease in measurable disease were observed (Table 1 and FIG. 3B)). After an initial rise, serum tALP levels steadily decreased, with tALP at 869 U/L at baseline and 197 U/L at Week 18 (FIG. 3B and Table 1). Hemoglobin increased 2.2 g/dL at Week 2 compared with baseline (Table 1). PSA decreased from 2.4 ng/mL at screening to 1.2 ng/mL at Week 18 (FIG. 3B and Table 1). The patient continues on Compound 1 treatment as of September 2010.

Discussion

All three patients experienced a striking decrease in uptake of radiotracer on bone scan upon treatment with Compound 1. These findings were accompanied by substantial reductions in bone pain and evidence of response or stabilization in soft tissue lesions during therapy with Compound 1. The onset of the effect was very rapid in two of the patients, with substantial improvement or near resolution of bone scan and improvement in pain occurring in the first 6 weeks. In the third patient, an apparent flare in the bone scan was observed at 6 weeks, followed by improvement by 12 weeks. To our knowledge, such a comprehensive and rapid impact on both osseous and soft tissue disease has not been observed in this patient population.

Uptake of radiotracer in bone depends on both local blood flow and osteoblastic activity, both of which may be pathologically modulated by the tumor cells associated with the bone lesion. Resolving uptake may therefore be attributable to either interruption of local blood flow, direct modulation of osteoblastic activity, a direct effect on the tumor cells in bone, or a combination of these processes. However, decreased uptake on bone scan in men with CRPC has only been rarely noted with VEGF/VEGFR targeted therapy, despite numerous trials with such agents. Similarly, observations of decreased uptake on bone scan in CRPC patients have only been reported rarely for abiraterone, which targets the cancer cells directly, and for dasatinib, which targets both cancer cells and osteoclasts. Thus, targeting angiogenesis alone, or selectively targeting the tumor cells and/or osteoclasts, has not resulted in effects similar to those observed in the patients treated with Compound 1.

These results indicate a potential critical role for the MET and VEGF signaling pathways in the progression of CRPC and point to the promise that simultaneously targeting these pathways may hold in reducing morbidity and mortality in this patient population.

Study 2: Effect of Compound 1 Administration on $NT^x$ Plasma Concentration

The effects of Compound 1 treatment on osteoclast activity was also investigated based on the measurement of changes in plasma concentration of the bone marker Cross-linked Cross-linked N-terminal telopeptides of type-1 collagen ($NT^x$) in CRPC patients (N=70). Bisphosphonate/denosumab treated patients with bone metastases and bisphosphonate/denosumab naïve patients with no known bone metastases were administered 100 mg Compound 1 daily. $NT^x$ plasma levels dropped in the majority of patients relative to baseline based on plasma samples analyzed at week 12 of the study. The results indicate the ability of Compound 1 to inhibit bone resorption.

Study 3: Effect of Compound 1 Administration on ALP Plasma Concentration

The effects of Compound 1 treatment on osteoclast activity was also investigated based on the measurement of changes in the plasma concentration of the bone marker alkaline phosphatase (ALP) in CRPC patients (N=61). Bisphosphonate/denosumab treated patients with bone metastases and bisphosphonate/denosumab naïve patients with no known bone metastases were administered 100 mg Compound 1 daily. ALP plasma levels dropped in the majority of patients relative to baseline based on plasma samples analyzed at week 12 of the study. The results indicate the ability of Compound 1 to inhibit bone resorption.

Study 4: Effect of Compound 1 Administration on Circulating Tumor Cell Plasma Concentration The effects of Compound 1 treatment on circulating tumor cell (CTC) concentration in CRPC patients. Patients with CRPC (N=59) were administered 100 mg Compound 1 daily. CTC plasma levels dropped in the majority of patients relative to baseline based on samples analyzed at week 6 or 12 of the study. The results indicate the ability of Compound 1 to inhibit tumor cell proliferation.

Study 5: Effect of Compound 1 Administration on $CT^x$ Plasma Concentration

The effects of Compound 1 treatment on osteoclast activity was also investigated based on the measurement of changes in plasma concentration of Cross-linked C-terminal telopeptides of type-1 collagen ($CT^x$) concentration in bisphosphonate treated and bisphosphonate naïve patients with CRPC that exhibited bone metastases (N=46). Cr levels dropped in the majority of patients relative to baseline based on plasma samples analyzed by ELISA at weeks 6 and 12 of the study. The results indicate the ability of Compound 1 to inhibit bone resorption.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A method of inhibiting bone resorption in the bones of patients with castration resistant prostate cancer that has metastasized to bone, comprising administering to the patients Compound 1:

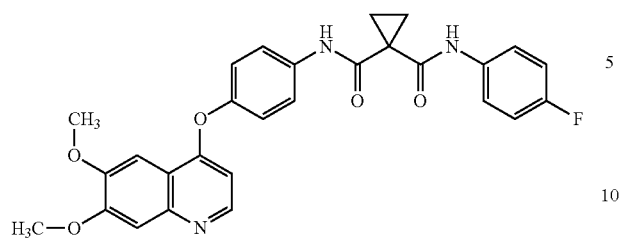
Compound 1
or a pharmaceutically acceptable salt thereof.
2. The method of claim 1, wherein Compound 1 is administered as the (L)- or (D)-malate salt.
3. The method of claim 1, wherein Compound 1 is administered as the (L)-malate salt.
* * * * *